US010309828B2

(12) United States Patent
Feitisch et al.

(10) Patent No.: US 10,309,828 B2
(45) Date of Patent: Jun. 4, 2019

(54) SPECTROMETER WITH ACTIVE BEAM STEERING

(71) Applicant: SpectraSensors, Inc., Rancho Cucamonga, CA (US)

(72) Inventors: Alfred Feitisch, Los Gatos, CA (US); Xiang Liu, Rancho Cucamonga, CA (US); Keith Benjamin Helbley, Rancho Cucamonga, CA (US); Douglas Beyer, Redlands, CA (US)

(73) Assignee: SpectraSensors, Inc., Rancho Cucamonga, CA (US)

( * ) Notice: Subject to any disclaimer, the term of this patent is extended or adjusted under 35 U.S.C. 154(b) by 0 days.

(21) Appl. No.: 15/730,548

(22) Filed: Oct. 11, 2017

(65) Prior Publication Data

US 2018/0128678 A1   May 10, 2018

Related U.S. Application Data

(63) Continuation of application No. 14/466,819, filed on Aug. 22, 2014, now Pat. No. 9,816,860.

(51) Int. Cl.
*G01J 3/02* (2006.01)
*G01J 3/42* (2006.01)
*G01N 21/31* (2006.01)

(52) U.S. Cl.
CPC .............. *G01J 3/0205* (2013.01); *G01J 3/027* (2013.01); *G01J 3/0237* (2013.01);
(Continued)

(58) Field of Classification Search
CPC ........ G01J 3/0205; G01J 3/0237; G01J 3/027; G01J 3/0278; G01J 3/0291; G01J 3/42; G01N 21/31
See application file for complete search history.

(56) References Cited

U.S. PATENT DOCUMENTS 5,929,981 A   7/1999   Keilbach
6,064,488 A   5/2000   Brand et al.
(Continued)

FOREIGN PATENT DOCUMENTS

DE        19840345 A1    3/2000
EP         0203767 A2   12/1986
WO    WO-2004/113887 A2   12/2004

OTHER PUBLICATIONS

Herriott, D., Kogelnik, H., and Kompfner, R. "Off-Axis Paths in Spherical Mirror Interferometers." *Applied Optics*, vol. 3, No. 4, 1964, pp. 523-526.
(Continued)

*Primary Examiner* — Hina F Ayub
(74) *Attorney, Agent, or Firm* — Christopher R. Powers; PatServe (57) ABSTRACT

A spectrometer includes a light source that emits a beam into a sample volume comprising an absorbing medium. Thereafter, at least one detector detects at least a portion of the beam emitted by the light source. It is later determined, based on the detected at least a portion of the beam and by a controller, that a position and/or an angle of the beam should be changed. The beam emitted by the light source is then actively steered by an actuation element under control of the controller. In addition, a concentration of the absorbing media can be quantified or otherwise calculated (using the controller or optionally a different processor that can be local or remote). The actuation element(s) can be coupled to one or more of the light source, a detector or detectors, and a reflector or reflectors intermediate the light source and the detector(s).

13 Claims, 7 Drawing Sheets

(52) U.S. Cl.
CPC .......... *G01J 3/0278* (2013.01); *G01J 3/0291* (2013.01); *G01J 3/42* (2013.01); *G01N 21/31* (2013.01); *G01J 2003/421* (2013.01); *G01N 2201/062* (2013.01); *G01N 2201/06113* (2013.01)

(56) References Cited

U.S. PATENT DOCUMENTS

| | | |
|---|---|---|
| 6,274,879 B1 | 8/2001 | Best-Timmann |
| 7,679,059 B2 | 3/2010 | Zhou |
| 9,518,866 B2 | 12/2016 | Feitisch et al. |
| 9,816,860 B2 | 11/2017 | Feitisch et al. |
| 2003/0094433 A1 | 5/2003 | Ouellet et al. |
| 2003/0190113 A1 | 10/2003 | Huang et al. |
| 2005/0128403 A1 | 6/2005 | Liu |
| 2005/0129840 A1 | 6/2005 | Lee et al. |
| 2005/0213092 A1 | 9/2005 | MacKinnon et al. |
| 2005/0229698 A1 | 10/2005 | Beecroft et al. |
| 2007/0246653 A1 | 10/2007 | Zhou |
| 2008/0239306 A1 | 10/2008 | Sutherland et al. |
| 2011/0066092 A1 | 3/2011 | Moeskops et al. |
| 2011/0140870 A1 | 6/2011 | Ullrich |
| 2011/0164251 A1 | 7/2011 | Richter |
| 2011/0239421 A1 | 10/2011 | Tertitski et al. |
| 2011/0299076 A1 | 12/2011 | Feitisch et al. |
| 2013/0077097 A1 | 3/2013 | Engstrand |
| 2014/0160474 A1 | 6/2014 | Keller et al. |
| 2014/0168649 A1 | 6/2014 | Smith |
| 2016/0066775 A1 | 3/2016 | Hunter et al. |
| 2016/0327479 A1 | 11/2016 | Feitisch et al. |

OTHER PUBLICATIONS

Herriott, Donald R. and Schulte, Harry J. "Folded Optical Delay Lines." *Applied Optics*, vol. 4, No. 8, 1965, pp. 883-889.

SPECTROMETER WITH ACTIVE BEAM STEERING

CROSS REFERENCE TO RELATED APPLICATIONS

The present application is a Continuation Application of U.S. patent application Ser. No. 14/466,819, entitled "SPECTROMETER WITH ACTIVE BEAM STEERING," and filed on Aug. 22, 2014, the disclosures of which are incorporated herein by reference in their entireties for all purposes.

TECHNICAL FIELD

The subject matter described herein relates to spectroscopic analyzers in which a beam emitted by a light source is selectively steerable using a controller.

BACKGROUND

Spectrometers use light emission or absorption or Raman scattering by matter to qualify and quantify specific atoms and molecules in analysis of gas, solid or liquid phase compounds. In one case, the radiation emitted from a light source is absorbed with a particular energy determined by optical transitions occurring within the atoms, ions or molecules of an analyte. In another case, the light emitted by atoms, ions or molecules of the analyte is composed of spectral components of particular energy, which are determined by optical transitions within the atoms or molecules. In yet another case, light scattered by matter contains spectral components which are created by Raman scattering, corresponding to certain particular transitions in molecules or ions. For example, in infrared absorption spectroscopy, discrete energy quanta are absorbed by molecules due to excitation of vibrational or rotational transitions of the intra-molecular bonds.

Variations in environmental conditions as well as aging or fouling of reflector surfaces in a spectrometer sample cell, or replacement of fouled or deteriorated reflector surfaces can cause a beam path of a light source within a spectrometer to change over time or as a result of changing a reflector. Changes of the beam path in an optical spectrometer can invalidate the spectrometer calibration. In most cases, such spectrometers require factory calibration of at least a sample cell or replacement by a skilled technician. Such service calls and factory repairs are costly and result in downtime for the spectrometer and the operation it controls, while such repairs are being performed. This is a common problem today with conventional TDL (tunable diode laser) spectrometers which require a factory calibration of the sample cell when at least one reflector in the cell has to be replaced due to fouling or due to other deterioration of a reflecting surface. The factory turn-around time of such a sample cell repair and replacement has been precluding TDL spectrometers being used in many petrochemical production processes, such as ethylene and propylene production, due to unavoidable reactor upset conditions, which result in liquids flowing through sample cells and leaving damaging residue on reflectors.

SUMMARY

In one aspect, an apparatus is provided that includes a light source, at least one detector, an actuation element, and a controller coupled to the actuation element. The light source is configured to emit a beam into a sample volume comprising an absorbing medium. The at least one detector is positioned to detect at least a portion of the beam emitted by the light source. The actuation element is configured to selectively cause the beam emitted by the light source to be steered. Concentration levels of the absorbing medium and the like can be determined based on the signal intensity detected by the at least one detector. In some variations, there can be two or more actuation elements.

The actuation element can be coupled to the light source, the at least one detector, a reflector intermediate the light source and the detector, and/or to at least one transmissive or reflective optical element intermediate the light source and the at least one detector. The actuation element can be coupled to a reflector and is configured to selectively cause at least one reflective property of the reflector to change.

The absorbing medium can be one or more of: gas, liquid, reflective media, emitting media, or Raman active media.

The apparatus can include a housing defining a sample volume. Such a housing can be, for example, a multiple-pass configuration in which the light is reflected between one or more optically reflective mirrors while the light remains inside the sample cell, a multiple-pass configuration in which the light is reflected and/or refracted by one or more optical elements while the light remains inside the sample cell, a Herriot Cell, an on-axis optical resonator, an elliptical light collector, an at least one reflection multipass cell, an off-axis optical resonator, a White cell, an optical cavity, a hollow core light guide, or a single pass configuration in which the light is not being reflected while the light remains inside the sample cell.

In other variations, the sample volume forms part of an open path system.

The actuation element can include at least one piezo element. In other variations, the actuation element includes one or more: stepper motors, electro-optical actuators, acousto-optical actuators, an adjustable optical waveguide, a micro-electro-mechanical systems (MEMS) actuation devices, a light valve, an inch-worm, a mechanical actuator, a magnetic actuator, an electrostatic actuator, an inductive actuator, a rotary actuator, a heated actuator, a pressure actuator, a stress and strain actuator, or an analog motor.

In some variations, the actuation element can include or be coupled to one or more of a prism, an etalon, a lens, gratings, a diffractive optical element, a reflector, a birefringent element, a crystal element, an amorphous element, an electro-optic element, an acousto-optic element, an optical window, an optical wedge, a waveguide, an electrically manipulated waveguide, or an air waveguide.

The controller can cause the light source to steer the beam in response to a position and/or an angle that such beam is detected by at least one detector. The beam (in response to signals from the controller) can be steered to a pre-defined position and angle along the at least one detector.

The at least one detector can include an array of photoreceivers and/or it can be a multi-element photoreceiver. The at least one detector can include at least one position sensing photodiode.

The light source can include at least one of a tunable diode laser, a tunable semiconductor laser, a quantum cascade laser, an intra-band cascade laser (ICL) a vertical cavity surface emitting laser (VCSEL), a horizontal cavity surface emitting laser (HCSEL), a distributed feedback laser, a light emitting diode (LED), a super-luminescent diode, an amplified spontaneous emission (ASE) source, a gas discharge laser, a liquid laser, a solid state laser, a fiber laser, a color center laser, an incandescent lamp, a discharge lamp, a thermal emitter, or a device capable of generating frequency tunable light through nonlinear optical interactions.

The at least one detector can include at least one of an indium gallium arsenide (InGaAs) detector, an indium arsenide (InAs) detector, an indium phosphide (InP) detector, a silicon (Si) detector, a silicon germanium (SiGe) detector, a germanium (Ge) detector, a mercury cadmium telluride detector (HgCdTe or MCT), a lead sulfide (PbS) detector, a lead selenide (Pb Se) detector, a thermopile detector, a multi-element array detector, a single element detector, a CMOS (complementary metal oxide semiconductor) detector, a CCD (charge coupled device detector) detector, or a photo-multiplier.

In another aspect, a light source emits a beam into a sample volume comprising an absorbing medium. Thereafter, at least one detector detects at least a portion of the beam emitted by the light source. It is then determined, based on the detected at least a portion of the beam and by a controller, that a position and/or an angle of the beam should be changed. An actuation element under control of a controller then causes the beam emitted by the light source to be selectively steered.

The actuation element can be coupled to the light source and cause a position and/or an angle of the light source to change. The actuation element can be coupled to the at least one detector and cause a position (along one or more of an x-axis, a y-axis, and a z-axis) and/or an angle (along one or more of an x-axis, a y-axis, and a z-axis) of the at least one detector to change. The actuation element can be coupled to at least one reflector positioned intermediate the light source and the at least one detector and cause a reflective property of the at least one reflector to change, including but not limited to angle, surface figure or radius of curvature and the like. The actuation element can be intermediate the light source and the at least one detector.

The actuation element can be coupled to at least one of a transmissive or reflective optical element intermediate the light source and the at least one detector. The actuation element in some variations can be coupled to two or more of: (i) the light source, (ii) the at least one detector, (iii) at least one reflector, or (iv) the at least one transmissive or reflective light beam actuation element intermediate the light source and the at least one detector.

Beam steering as provided herein can include (unless otherwise specified) changing an overall beam path length. For example, the at least one actuation element can cause one or more of a reflector, the light source, a transmissive element, the at least one detector to translate along a z-axis to change the overall beam path length.

In another aspect, a light source is caused to emit a beam into a sample volume comprising an absorbing medium. Thereafter, a signal is received from at least one detector that characterizes detection of at least a portion of the beam emitted by the light source. It is then determined, based on the received signal, that a position and/or an angle of the beam should be changed. In response, an actuation element is caused to selectively steer the beam emitted by the light source.

The subject matter described herein provides many technical advantages. For example, degradation of spectrometer calibration fidelity and calibration offsets due to age and environmental factors or due to reflector exchanges can be greatly reduced by selectively steering the beam(s) which are emitted by a light source or which are received by a detector to ensure optimal performance and calibration fidelity. In particular, with the current subject matter spectrometers can be repaired in the field by replacing fouled or damaged components, without need for factory realignment and recalibration. Furthermore, by providing active beam steering, the current subject matter can be used to maintain optimum optical throughput through a spectrometer thereby extending an amount of time required between cleaning intervals. Furthermore, active beam steering as provided herein can be used to counter external influences such as temperature changes in the sample gas and/or the environment, thermal expansion, index changes, Schlieren effects, and the like which can cause the beam path to alter.

Non-transitory computer program products (i.e., physically embodied computer program products) are also described that store instructions, which when executed by one or more data processors of one or more computing systems, causes at least one data processor to perform operations herein. Similarly, computer systems are also described that may include one or more data processors and memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. It should be noted that the current subject matter contemplates both a closed sample cell and an open path system for detecting trace gases and/or liquids. The terms "sample gas volume", "gas volume", "sample liquid volume" and "liquid volume" as used herein therefore refers to either a flowing volume or a static, batch volume of gas or liquid (as the case may be).

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

To address the aforementioned and other potential issues due to beam position sensitivity with spectroscopic measurements, implementations of the current subject matter can provide a spectrometer having a light source with the ability to actively steer its beam(s) or a portion thereof on its path through a measurement sample onto a detector. As used herein (unless otherwise specified), steering refers to changing the angle of the beam path, the length of the beam path, and/or a position or angle of a device forming part of a spectrometer. Gas and/or liquid sampled from a source can include absorbing media (e.g., one or more analyte compounds, etc.). Detection and/or quantification of the concentration of such absorbing media can be performed by spectroscopic analysis. The spectrometer can include at least one actuation element that causes a beam path of the beam(s) emitted by the light source to change as specified by a controller. In some variations, the system can include spatial detectors/detector arrays so that a control unit can determine a spatial and/or an angular position of the beam and cause the actuation element to make any required changes.

Analyte compounds with which implementations of the current subject matter can be used include, all gas, liquid and solid phase atoms, molecules and ions, which absorb light, but are not limited to, hydrogen sulfide ($H_2S$); hydrogen chloride (HCl); water vapor ($H_2O$); hydrogen fluoride (HF); hydrogen cyanide (HCN); hydrogen bromide (HBr); ammonia ($NH_3$); arsine ($AsH_3$); phosphine ($PH_3$); oxygen ($O_2$); carbon monoxide (CO); carbon dioxide ($CO_2$); chlorine ($Cl_2$); nitrogen ($N_2$); hydrogen ($H_2$); hydrocarbons, including but not limited to methane ($CH_4$), ethane ($C_2H_6$), ethylene ($C_2H_4$), acetylene($C_2H_2$), etc.; fluorocarbons; chlorocarbons; alcohols; ketons; aldehydes; acids, bases and the like.

Figure 1:
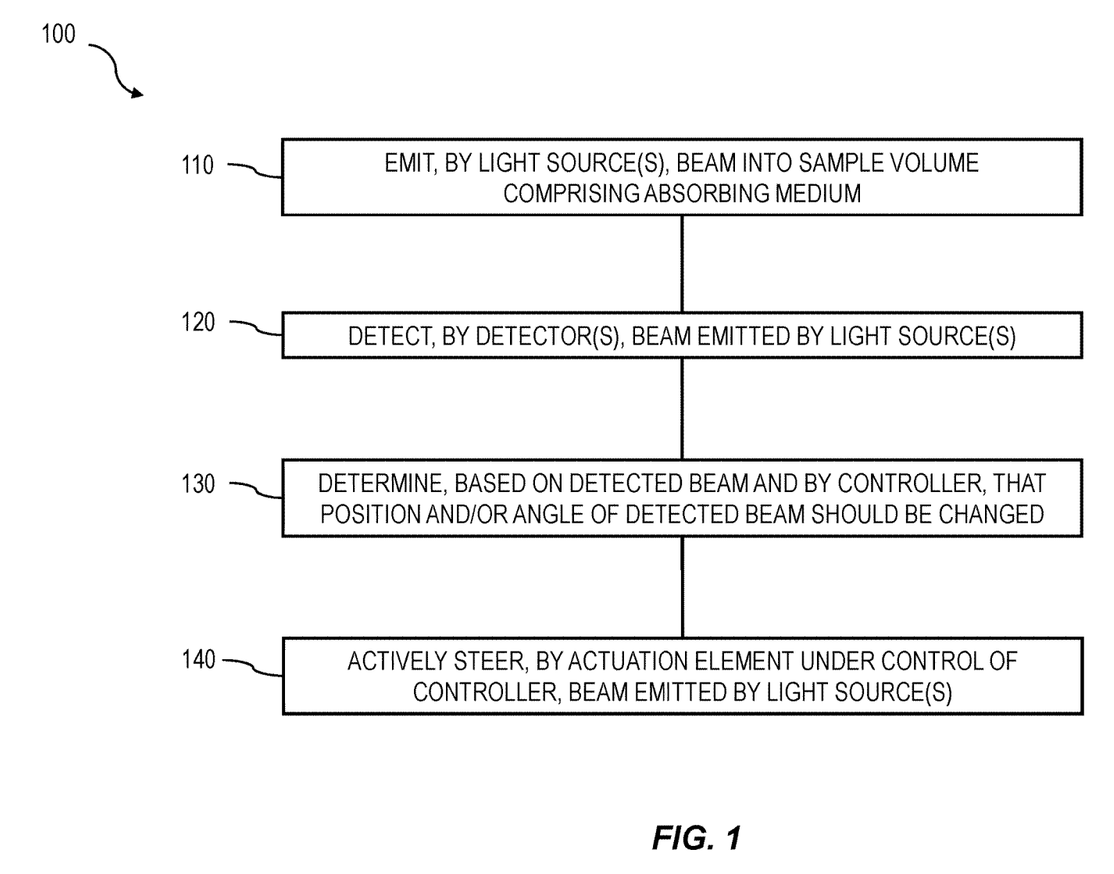
FIG. 1 is a process flow diagram illustrating selective steering of a beam within a spectrometer.

FIG. 1 is a process flow diagram 100 in which, at 110, a light source emits a beam into a sample volume comprising an absorbing medium. Thereafter, at 120, at least one detector detects at least a portion of the beam emitted by the light source. It is later determined, at 130, based on the detected at least a portion of the beam and by a controller, that a position and/or of the beam as detected by the detector should be changed. The beam emitted by the light source is then, at 140, actively steered by at least one actuation element under control of the controller. In addition, a concentration of the absorbing media can be quantified or otherwise calculated (using the controller or optionally a different processor that can be local or remote). The actuation element(s) can be coupled to one or more of the light source, a detector or detectors, and a reflector or reflectors intermediate the light source and the detector(s) (although it will be appreciated that a reflector is not required for all variations).

FIGS. 2-7 are diagrams 200-700 that show example spectrometers for implementing the current subject matter. While the following is described in connection with detecting absorbing media within gas, it will be appreciated that the current subject matter can also be applied to detecting absorbing media within liquid. A light source 205 provides a continuous or pulsed light that is directed to a detector 210 via a path length 215. The light source 205 can include, for example, one or more of a tunable diode laser, a tunable semiconductor laser, a quantum cascade laser, an intra-band cascade laser (ICL), a vertical cavity surface emitting laser (VCSEL), a horizontal cavity surface emitting laser (HCSEL), a distributed feedback laser, a light emitting diode (LED), a super-luminescent diode, an amplified spontaneous emission (ASE) source, a gas discharge laser, a liquid laser, a solid state laser, a fiber laser, a color center laser, an incandescent lamp, a discharge lamp, a thermal emitter, and the like. The detector 210 can include, for example, one or more of an indium gallium arsenide (InGaAs) detector, an indium arsenide (InAs) detector, an indium phosphide (InP) detector, a silicon (Si) detector, a silicon germanium (SiGe) detector, a germanium (Ge) detector, a mercury cadmium telluride detector (HgCdTe or MCT), a lead sulfide (PbS) detector, a lead selenide (Pb Se) detector, a thermopile detector, a multi-element array detector, a single element detector, a photo-multiplier, a CMOS (complementary metal oxide semiconductor) detector, a CCD (charge coupled device detector) detector and the like.

Figure 2:
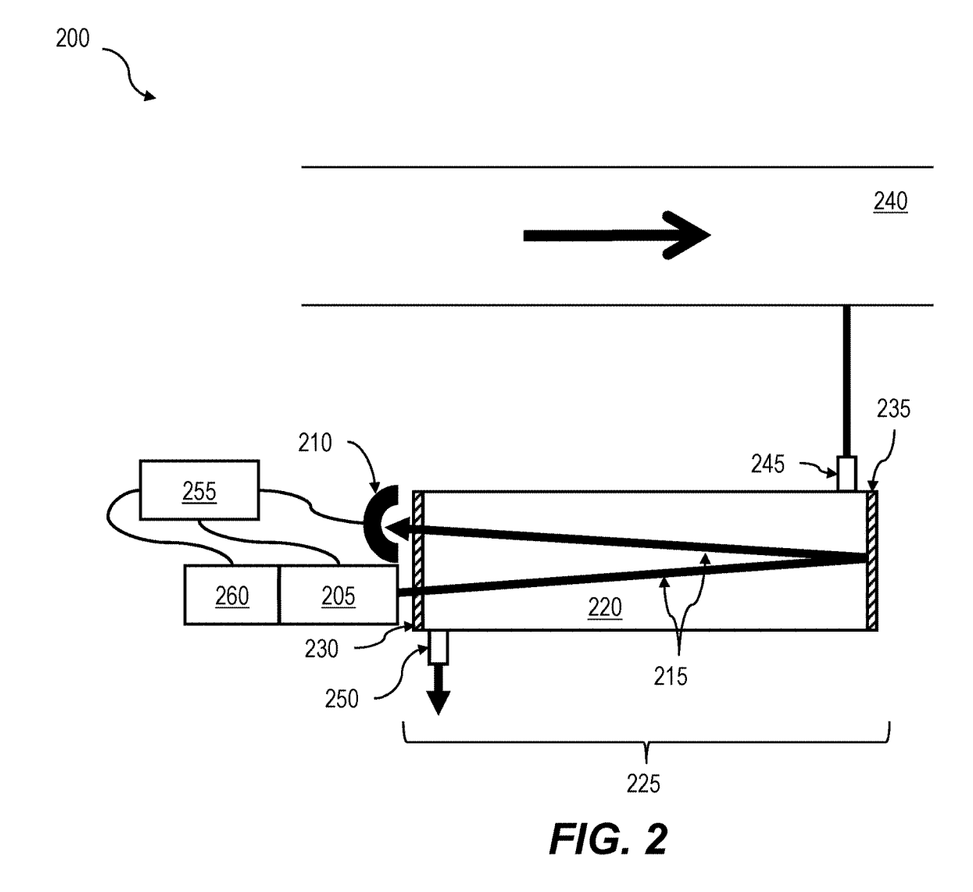
FIG. 2 is a diagram illustrating a first spectrometer with a sample cell.
Figure 3:
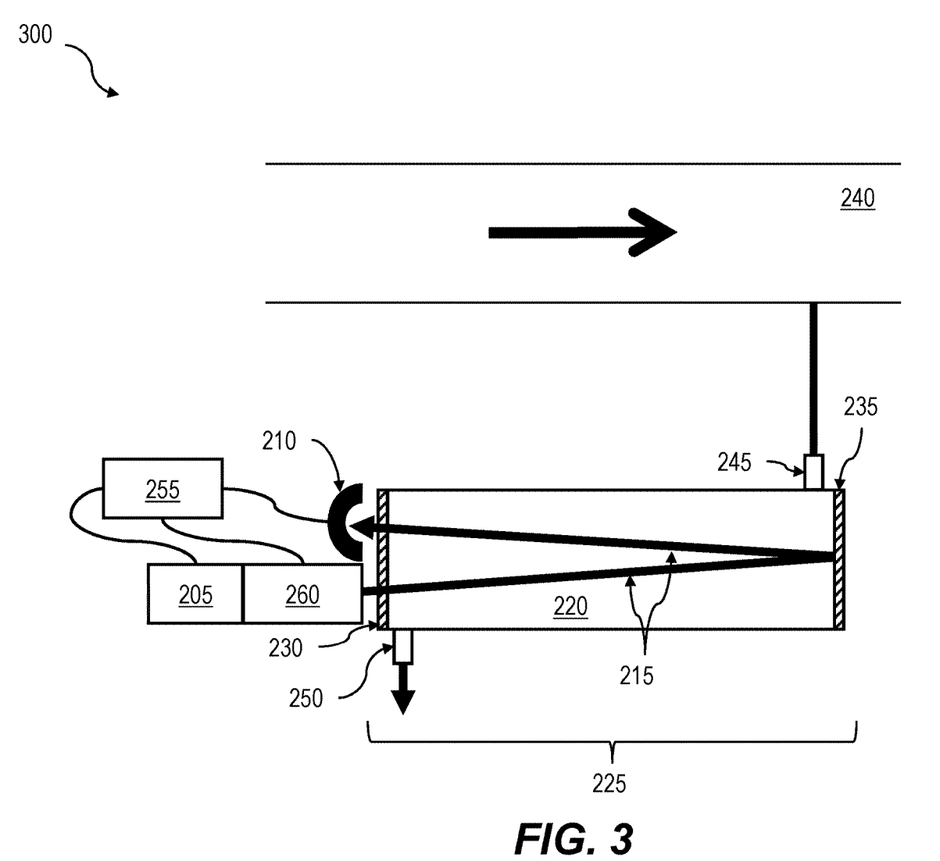
FIG. 3 is a diagram illustrating a second spectrometer with a sample cell.

The path length 215 can traverse one or more volumes. In the example systems 200-500 shown in FIGS. 2-7, the path length 215 can twice traverse a volume 220 of an optical cell 225 that includes a window or other at least partially radiation transmissive surface 230 and a reflector (e.g., a mirror, etc.) 235 or other at least partially radiation reflective surface that at least partially defines the volume 220. Sample gas can, in some implementations, be obtained from a gas source, which in the examples of FIGS. 2 and 3 is a pipeline 240, for delivery to the volume 220, for example via a sample extraction port or valve 245 that receives the sample gas from the source. Gas in the volume 220 can exit via a second outlet valve or port 250.

Figure 4:
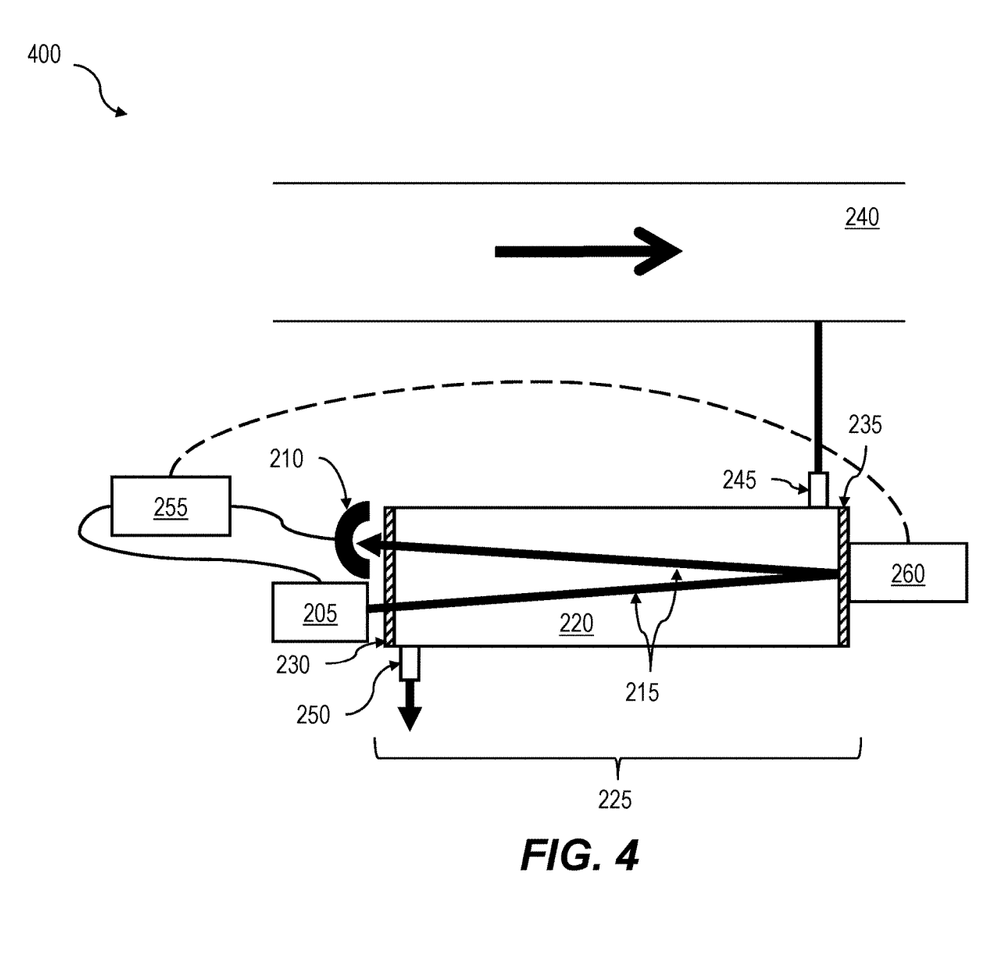
FIG. 4 is a diagram illustrating a third spectrometer with a sample cell.
Figure 5:
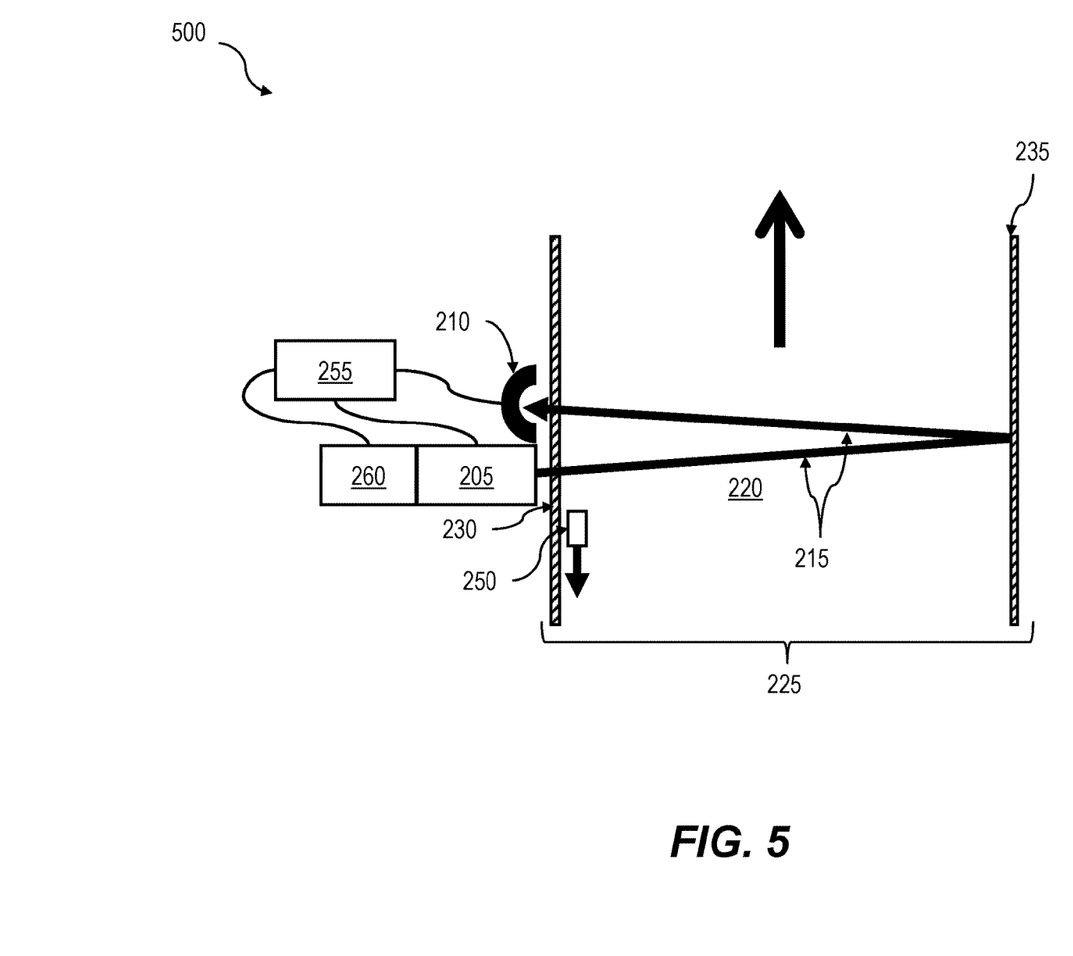
FIG. 5 is a diagram illustrating a first open path spectrometer.
Figure 6:
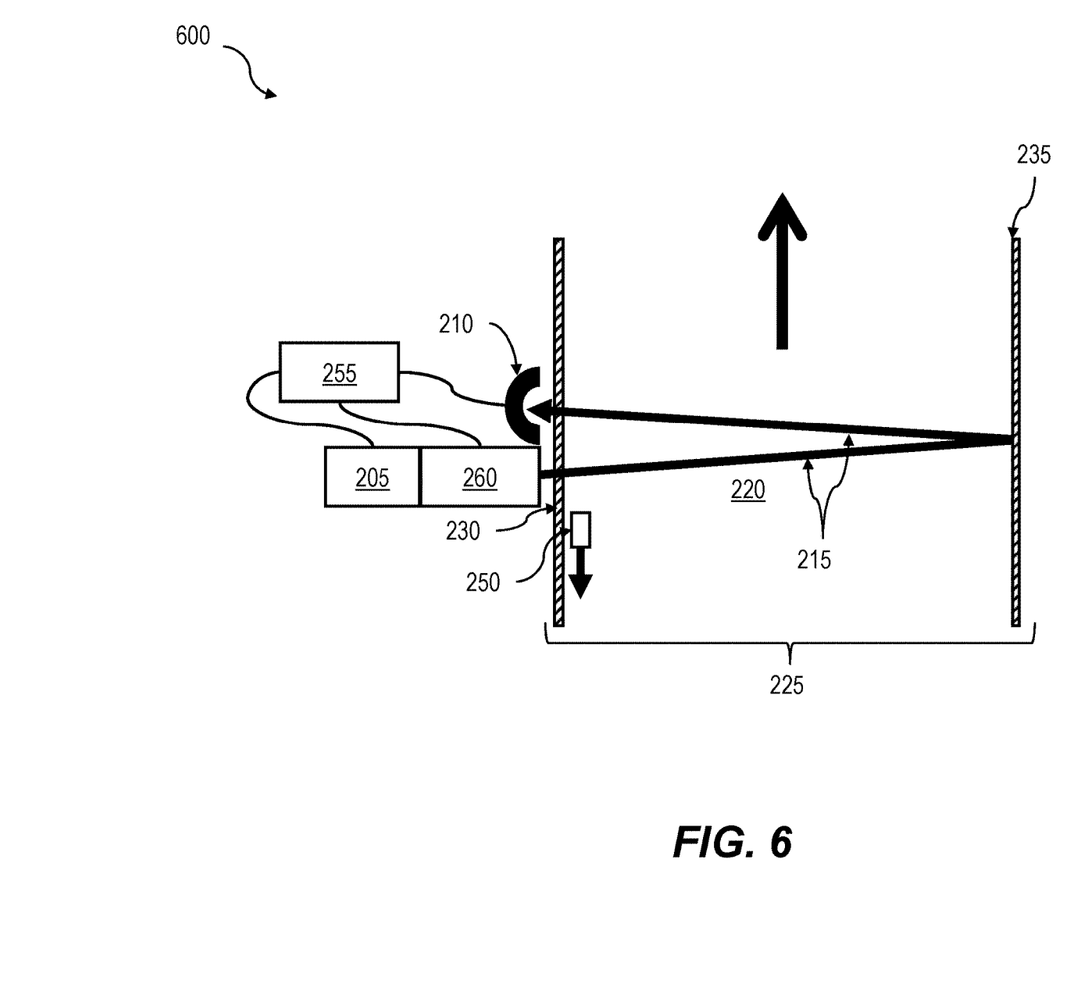
FIG. 6 is a diagram illustrating a second open path spectrometer.
Figure 7:
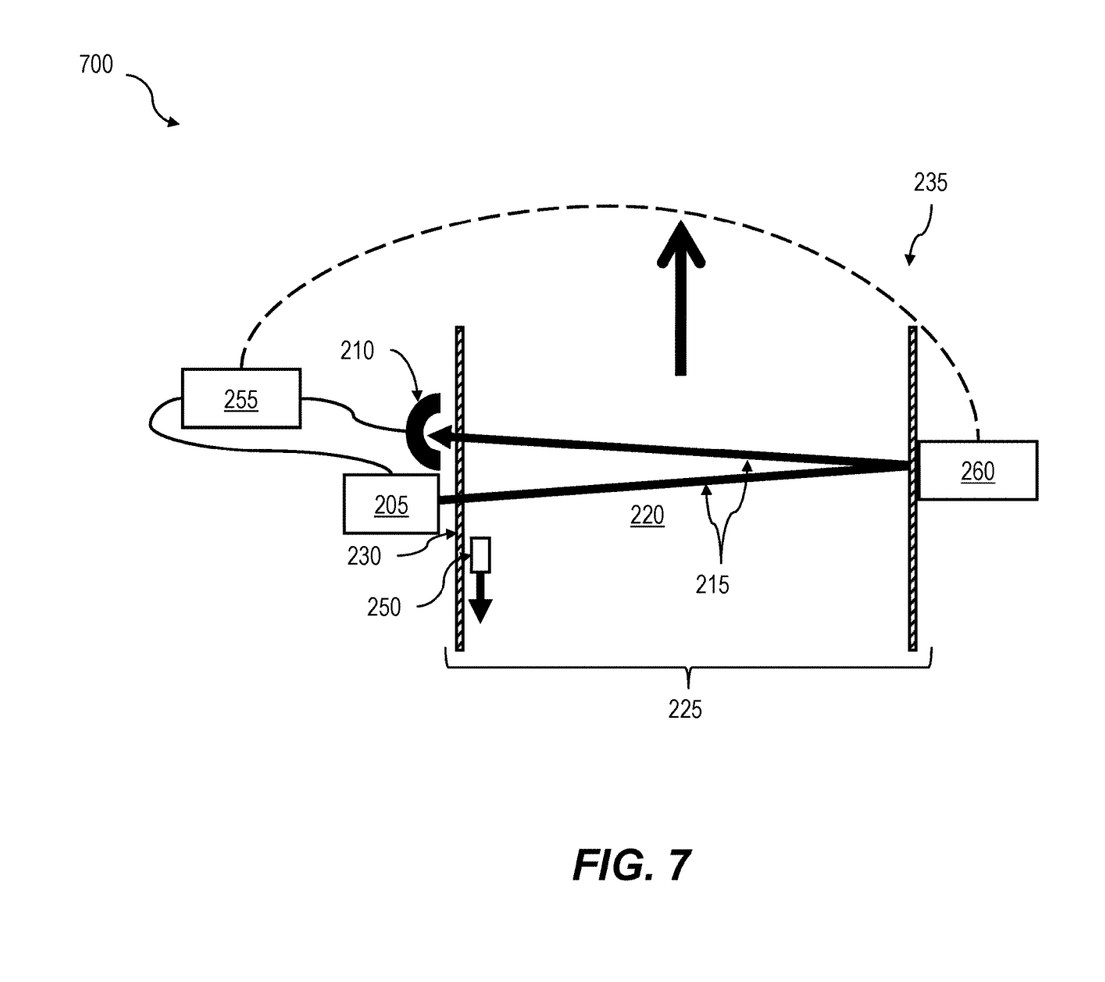
FIG. 7 is a diagram illustrating a second open path spectrometer.

As illustrated in FIGS. 2-4, in some variations, the volume 220 can be part of a housing that defines a sample cell that can be, for example, one or more of a Herriott Cell, an off-axis optical resonator, an on-axis optical resonator, an elliptical light collector, a White cell, an optical cavity, a hollow core light guide, a multiple pass configuration in which the light beam is reflected at least once or a single pass configuration in which the light is not being reflected while the light traverses the sample cell. In other variations, as illustrated in FIGS. 5-7, the volume 220 can be part of an open path system that does not include a dedicated sample cell. Open path systems can be used for various applications including atmospheric pollutant studies, fence line monitoring, process line/tank leak detection, industrial gas-purity applications, and monitoring and control of combustion processes, especially on exhaust stacks.

A controller 255, which can include one or more programmable processors or the like, can communicate with one or more of the light source 205, the detector 210, and the reflector 235 for controlling the emission of the light 215 and receiving signals generated by the detector 210 that are representative of the intensity of light impinging on the detector 210 as a function of wavelength. In various implementations, the controller 255 can be a single unit that performs both of controlling the light source 205 and receiving signals from the detector 210, or it can be more than one unit across which these functions are divided. Communications between the controller 255 or controllers and the light source 205 and detector 210 can be over wired communications links, wireless communications links, or any combination thereof. The controller 255 can also, in some cases, be used to quantify an amount of absorbing media using the signal generated by the detector 210. In other variations, the quantification can be determined by at least one remote data processor.

An actuation element 260 (or two or more actuation elements 260) can be coupled to one or more of (i) the light source 205, (ii) the detector 210, or (iii) the reflector 235, and the controller 255. The controller 255 can send a signal to the actuation element 260 to cause it to selectively steer (i.e., change trajectory of, etc.) the beam emitted by the light source 205 as detected by the detector 210. In some variations, the actuation element 260 can be any device that causes a position of the light source 205 to physically move and/or its beam angle to physically change (and as such the actuation element 260 is not intermediate either of the beam path, on one hand, and the light source 205 and the detector 210, on the other hand). For example, with this variation, the actuation element 260 can be/include at least one piezo actuator element, an inch-worm, a mechanical actuator, a magnetic actuator, an electrostatic actuator, an inductive actuator, a rotary actuator, a heated actuator, a pressure actuator, a stress and strain actuator, an analog motor, a stepper motor, an electro-optical actuator, an acousto-optical actuator, an adjustable wave guide and/or a micro-electro-mechanical systems (MEMS) actuation device. Such actuation elements 260 can cause at least a portion of the light source 205 to move along the x-axis, the y-axis, the z-axis (or a combination of two or more dimensions). With this variation, location of the beam origin (laser location) can be changed with respect to the sample cell (having an entrance hole and an exit hole).

In some variations, the actuation element 260 can be any device that causes a position and/or the angle of the detector 210 to physically move (and as such the actuation element 260 is not intermediate either of the beam path, on one hand, and the light source 205 and the detector 210, on the other hand). For example, with this variation, the actuation element 260 can be/include at least one piezo actuator element, an inch-worm, a mechanical actuator, a magnetic actuator, an electrostatic actuator, an inductive actuator, a rotary actuator, a heated actuator, a pressure actuator, a stress and strain actuator, an analog motor, a stepper motor, an electro-optical actuator, an acousto-optical actuator, an adjustable waveguide and/or a micro-electro-mechanical systems (MEMS) actuation device. Such actuation elements 260 can cause at least a portion of the detector 210 to move along the x-axis, the y-axis, the z-axis (or a combination of two or more dimensions). Movement along the z-axis can cause the overall beam length to be changed (reduced or increased).

In addition or in the alternative (as shown in FIGS. 3 and 6), the actuation element 260 can be placed intermediate the light source 205 and the detector 210 and/or to intersect the beam path. With such an arrangement, the actuation element 260 can be any device/element that optically causes at least a portion of the beam emitted by the light source 205 to selectively move and/or change its beam angle (in some cases without moving the light source 205). With this latter variation, the actuation element 260 can be/include/be coupled to at least one of a prism, an etalon, a lens and/or gratings, a diffractive optical element, a reflector, a birefringent element, a crystal element, an amorphous element an electro-optic element, an acousto-optic element, an optical window, an optical wedge, and a waveguide such as an electrically manipulated waveguide (e.g., solid state waveguides in which refractive index patterns can be changed by applying localized electrical fields and/or currents, etc.) or an air waveguide. With regard to the latter, an air waveguide refers to manipulation of the refractive index of air using one or more lasers or other light sources (for example, by selectively pulsing the laser(s) to heat air, etc.) which can, in turn, be used for beam steering. Some or all of the actuation elements 260 can move in at least one of x-axis, the y-axis, or the z-axis.

As described above, in some variations, the reflector(s) 235 can be translated in x,y, and/or z direction or its angle can be changed with respect to the incident light beam and/or their reflective properties, including but not limited to radius of curvature and surface figure at the location of the incident light beam can change to steer the beam emitted by the light source 205. For example, an actuation element 260 can be/include at least one piezo actuator element, an inch-worm, a mechanical actuator, a magnetic actuator, an electrostatic actuator, an inductive actuator, a rotary actuator, a heated actuator, a pressure actuator, a stress and strain actuator, an analog motor, a stepper motor, an electro-optical actuator, an acousto-optical actuator, an adjustable waveguide and/or a micro-electro-mechanical systems (MEMS) actuation device can cause the position and/or the angle of the reflector 235 to change (which in turn changes the position of the beam path). In other cases, the reflector 235 can comprise adaptive optics having actuable reflecting surfaces. Such an adaptive optical element can be a reflector made from a thin reflecting foil, with the actuation element 260 mounted or printed onto the backside of the reflector 235 in a multiplicity of locations. Such mirrors can provide for active changes of the reflecting surface in arbitrary fashion which, in turn, allows for steering of the beam emitted by the light source 205 (via the controller 255).

In some variations, the controller 255 can make a determination that a beam path should be steered based on an intensity level detected by the detector 210 without reference to spatial location of such beam. For example, the intensity level can indicate that a center of the beam has diverged and/or that there is some optical diffraction or interference along the beam path. The intensity level detected by the detector 210 can be compared to a single intensity value at a single light frequency and/or detected intensity can be compared to a frequency profile (which can be generated during calibration of the spectrometer, etc.). Deviations from such preset frequency or the frequency profile can be used to trigger beam steering.

In addition or in the alternative, the controller 255 can make a determination that a beam path should be steered based on a position of the beam as detected by the detector 210. With such latter variations, an array of photoreceivers and/or a detector with an array of cells can be used. For example, the detector 210 can be a quad cell detector and/or a position sensing photodiode, or a linear or 2D array of photoreceivers. With the example of a quad cell detector, the position of the center point of the emitted beam can be determined by a comparison of the detected signals from each cell. Horizontal position of the center point can be calculated by $[(cell_2+cell_4)-(cell_1+cell_3)]/(cell_1+cell_2+cell_3+cell_4)$ and the vertical position of the center point can be calculated by $[(cell_1+cell_2)-(cell_3+cell_4)]/(cell_1+cell_2+cell_3+cell_4)$. In another example, the position sensitive detector can be a detector which detects the x and y position as well as the x and y angles of the beam. Furthermore, a multi-element linear detector array can be used to determine the beam position. In another variation, a 2-dimensional detector array can be used to determine the beam position. With such spatially sensitive detectors, a pre-defined position (along two or more dimensions) and/or pre-defined angle (as specified by two or more dimensions) can be maintained via the controller 255 and the actuation element 260.

The volume 220 can be maintained at a stable temperature and pressure. Alternatively, the volume 220 can include one or more temperature and/or pressure sensors to determine a current temperature and pressure within that volume for use in one or more calculations to compensate for temperature and/or pressure changes relative to a validation or calibration condition of the spectroscopic instrument. Furthermore, the volume 220 can be adjusted to preset temperature and pressure by heating elements and pressure control elements or mass flow controllers.

The controller 255, or alternatively one or more other processors that are either collocated with the other components or in wireless, wired, etc. communication therewith, can perform the processing functions discussed above in reference to the method illustrated in FIG. 1.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. An apparatus comprising:
a light source configured to emit a beam into a channel comprising an absorbing medium, wherein the light source is a tunable diode laser;
at least one detector positioned to detect at least a portion of the beam emitted by the tunable diode laser, wherein the tunable diode laser and the detector are positioned on opposing sides of the channel in an open path configuration;
at least one actuation element configured to selectively cause the beam emitted by the tunable diode laser to be steered; and
a controller coupled to the at least one actuation element, the controller configured to: determine that a path of the beam should be steered based on at least one of an intensity level and a position of the beam detected by the at least one detector; identify a divergence of the path of the beam and/or optical diffraction and/or an interference along the path of the beam; and cause the at least one actuation element to steer the beam to adjust the position and/or an angle of the beam to correct the divergence and/or the optical diffraction and/or the interference along the path of the beam in response to the position and/or an angle of the beam that is detected by the detector.

2. The apparatus of claim 1, wherein the at least one actuation element is coupled to the light source and/or the at least one detector.

3. The apparatus of claim 1, wherein the at least one actuation element is coupled to a transmissive optical element and/or a reflective optical element.

4. The apparatus of claim 1, wherein the absorbing medium comprises a gas, a liquid, a reflective media, an emitting media, and/or a Raman active media.

5. The apparatus of claim 1, wherein the at least one actuation element comprises at least one piezo element.

6. The apparatus of claim 1, wherein the at least one actuation element comprises a stepper motor, an electro-optical actuator, an acousto-optical actuator, a micro-electro-mechanical systems (MEMS) actuation device, an inchworm, a mechanical actuator, a magnetic actuator, an electrostatic actuator, an inductive actuator, a rotary actuator, a heated actuator, a pressure actuator, a stress and strain actuator, and/or an analog motor.

7. The apparatus of claim 1, wherein the at least one actuation element comprises or is coupled to a prism, an etalon, a lens, one or more gratings, a diffractive optical element, a reflector, a birefringent element, a crystal element, an amorphous element, an electro-optic element, an acousto-optic element, an optical window, an optical wedge, a waveguide, an adjustable waveguide, an electrically manipulated waveguide, and/or an air waveguide.

8. The apparatus of claim 1, wherein the steering of the beam comprises adjusting the position of the beam in accordance with a pre-defined x-y position and/or adjusting the angle of the beam in accordance with a pre-defined x-y angle.

9. The apparatus of claim 1, wherein the controller is further configured to cause the at least one actuation element to maintain the position of the beam at a pre-defined x-y position and/or maintain the angle of the beam at a pre-defined x-y angle.

10. The apparatus of claim 1, wherein the at least one detector comprises an array of photoreceivers, a multi-element photoreceiver, and/or at least one position sensing photodiode.

11. The apparatus of claim 1, wherein the at least one detector comprises an indium gallium arsenide (InGaAs) detector, an indium arsenide (InAs) detector, an indium phosphide (InP) detector, a silicon (Si) detector, a silicon germanium (SiGe) detector, a germanium (Ge) detector, a mercury cadmium telluride detector (HgCdTe or MCT), a lead sulfide (PbS) detector, a lead selenide (PhSe) detector, a thermopile detector, a multi-element array detector, a single element detector, a CMOS (complementary metal oxide semiconductor) detector, a CCD (charge coupled device detector) detector, and/or a photo-multiplier.

12. The apparatus of claim 1, wherein steering of the beam comprises changing an overall beam path length.

13. A method comprising:
  emitting, by a tunable diode laser, a beam into a channel comprising an absorbing medium;
  traversing the channel by the beam a single time in an open path system configuration;
  detecting, by at least one detector, at least a portion of the beam emitted by the tunable diode laser;
  determining, by a controller, that a path of the beam should be steered based on at least one of an intensity level and a position of the beam, the determining comprising identifying a divergence in the path of the beam, an optical diffraction along the path of the beam, and/or the interference along the path of the beam; and
  selectively steering, by at least one actuation element coupled with the controller, the beam to adjust the position and/or an angle of the beam, the position and/or the angle of the beam being adjusted in order to correct the divergence, the optical diffraction, and/or the interference, the beam being steered in response to the position and/or the angle of the beam that is detected by the detector.

\* \* \* \* \*